United States Patent
Kondo et al.

(10) Patent No.: US 6,331,628 B1
(45) Date of Patent: Dec. 18, 2001

(54) PROCESS FOR THE PREPARATION OF BENZONITRILE COMPOUNDS

(75) Inventors: Yasuo Kondo; Yasuhisa Sugiyama; Norio Tanaka, all of Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/536,680

(22) Filed: Mar. 28, 2000

(30) Foreign Application Priority Data

Mar. 29, 1999 (JP) .................................................. 11-086230

(51) Int. Cl.$^7$ .................................................. C07D 239/54
(52) U.S. Cl. .................................................. 544/312
(58) Field of Search .......................................... 544/312

(56) References Cited

U.S. PATENT DOCUMENTS

| | | |
|---|---|---|
| 4,211,721 | 7/1980 | Cotter . |
| 4,285,883 | 8/1981 | Yoshikawa . |
| 5,127,935 | * 7/1992 | Satow et al. ............................. 71/92 |
| 5,356,863 | * 10/1994 | Satow et al. ......................... 504/243 |
| 5,917,079 | 6/1999 | Chong et al. . |
| 5,965,766 | 10/1999 | Chong et al. . |

FOREIGN PATENT DOCUMENTS

| | | |
|---|---|---|
| 0 384 392 | 8/1990 | (EP) . |
| 0 613 719 | 9/1994 | (EP) . |
| 56-79662 | 6/1981 | (JP) . |
| 2-42051 | 2/1990 | (JP) . |
| 3-14554 | 1/1991 | (JP) . |
| 4-169564 | 6/1992 | (JP) . |
| 5-186436 | * 7/1993 | (JP) . |
| 9-48761 | 2/1997 | (JP) . |
| 10-139770 | 5/1998 | (JP) . |
| 10-265449 | 10/1998 | (JP) . |

OTHER PUBLICATIONS

B. A. Anderson, et al., J. Org. Chem., vol. 63, No. 23, pp. 8224–8228, "Cooperative Catalyst Effects in Palladium-–Mediated Cyanation Reations of Aryl Halides and Triflates", 1998.

L. Cassar, Journal of Organometallic Chemistry, pp. C–57 to C–58, "A New Nickel–Catalyzed Syntesis of Aromatic Nitriles", 1973.

L. Cassar, et al., Adv. Chem. Ser., vol. 132, pp. 252–273, "Nickel–Catalyzed Cyanation of Aromatic Halides", 1973.

J. R. Dalton, et al., J. Org. Chem., vol. 44, No. 24, pp. 4443–4444, "Alumina–Assisted Aryl Cyanation", 1979.

T. Okano, et al., Synlet Letters, pp. 243–244, "Catalytic Cyanation of Aryl Halides with NACN in the Presence of Crowned Phosphine Complexes of Palladium under Solid–Liquid Two–Phase Conditions", 1998.

T. Okano, et al., Chemistry Letters, pp. 425–426, "Biphasic Cynation of Aryl Halides with Counter Phase Tranfer Catalysts", Feb. 9, 1998.

M. Prochazka, et al., Collection Czechoslovak Chem. Commun., vol. 48, pp. 1765–1773, "Preparation of Unsaturated Nitriles", 1983.

Y. Sakakibara, et al., Bull. Chem. Soc. Jpn, vol. 61, No. 6, pp. 1985–1990, "The Cyanation of Aromatic Halides Catalyzed by Nickel(0) Complexes Generated in Situ. I. General Scope and Limitations", Jun. 1988.

K. Tagagi, Bull. Inst. Chem. Res., vol. 67, No. 3, pp. 136–138, "Cyanation of Iodobenzene Catalyzed by $Pd_2(dba)_3 \cdot CHCl_3$", 1989.

K. Takagi, et al., Chemistry Letters, pp. 471–474, "Palladium(II) Catalyzed Synthesis of Aryl Cyanides from Aryl Halides", 1973.

K. Takagi, et al., Bull. Chem. Soc. Jpn., vol. 64, No. 4 pp. 1118–1121, "Nucleophilic Displacement Catalyzed by Transition Metal. IX. 1 $[Pd_2(dba)_3]$. $CHCl_3$–DPPF Catalyzed Cyanation of Aryl Halides and Aryl Triflates", 1991.

K. Takagi, et al., Bulletin of the Chemical Society of Japan, vol. 48, No. 11, pp. 3298–3301, "Nucleophilic Displacement Catalyzed by Transition Metal.I. General Consideration of the Cyanation of Aryl Halides Catalyzed by Palladium (II)", 1975.

* cited by examiner

*Primary Examiner*—John M. Ford
*Assistant Examiner*—Thomas McKenzie
(74) *Attorney, Agent, or Firm*—Oblon, Spivak, McClelland, Maier & Neustadt, P.C.

(57) ABSTRACT

A novel process for the preparation of benzonitrile compounds useful for herbicides or their intermediates is provided. A process for the preparation of compounds of the formula (1), characterized in comprising reacting a compound of the formula (1a) with one or more cyanides selected from potassium cyanide, sodium cyanide and zinc cyanide in the presence of a metallic catalyst.

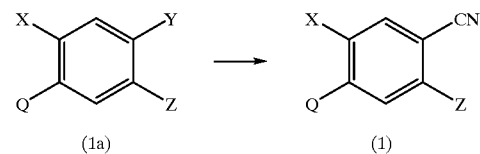

(1a)        (1)

In the scheme, X is hydrogen, fluorine or chlorine atom; Z is nitro, amino or $C_1$–$C_4$ alkylsulfonylamino group or the like; Y is fluorine, chlorine or bromine atom or the like; and Q is hydrogen atom, or nitro or amino group or the like.

16 Claims, No Drawings

PROCESS FOR THE PREPARATION OF BENZONITRILE COMPOUNDS

BACKGROUND OF THE INVENTION

1. Field of the Invention

The present invention relates to a process for the preparation of benzonitrile compounds as described in U.S. Pat. No. 5,127,935 and JP-5-186436A, which are useful as herbicides and their intermediates.

2. Description of the Background

A process for the preparation of benzonitrile compounds is described in JP-9-48761A. Since the process includes the use of copper cyanide as a cyanizing agent, the industrial application thereof has the following problems. The treatment of a waste fluid is troublesome since the waste fluid contains copper which is one of the metals designated in Water Pollution Control Law. In addition, copper cyanide is expensive. Accordingly, the improvement of the above process has been demanded.

SUMMARY OF THE INVENTION

The present inventors concentrated on developing another process for the preparation of benzonitrile compounds useful as herbicides and their intermediates so as to solve the above problems. As the result, it was found that the benzonitrile compound can be obtained with a high yield by synthesizing it in the presence of a metallic catalyst even if potassium, sodium or zinc cyanide, which has a reactivity lower than that of copper cyanide, is used as a cyanizing agent. Thus, the present invention relates to the process for the preparation set forth below.

[1] A process for the preparation of benzonitrile compounds represented by the formula (1):

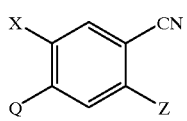

(1)

wherein

X is hydrogen, fluorine or chlorine atom;

Z is nitro, amino, $C_1$–$C_4$ alkylsulfonylamino, bis($C_1$–$C_4$ alkylsulfonyl)amino, ($C_2$–$C_5$ alkoxycarbonyl)amino, ($C_2$–$C_5$ alkylcarbonyl)amino, (optionally substituted benzoyl)amino, ($C_2$–$C_5$ alkylcarbonyl)($C_1$–$C_4$ alkylsulfonyl)amino or (optionally substituted benzoyl)($C_1$–$C_4$ alkylsulfonyl)amino group; and Q is hydrogen atom, or nitro, amino, ($C_2$–$C_5$ alkoxycarbonyl)amino, 6-trifluoromethyl-2,4(1H,3H)-pyrimidinedione-3-yl, 1-methyl-6-trifluoromethyl-2,4(1H,3H)pyrimidinedione-3-yl or 1-amino-6-trifluoromethyl-2,4(1H,3H)pyrimidinedione-3-yl group, provided that if Z is nitro or amino group, then Q is ($C_2$–$C_5$ alkoxycarbonyl)amino, 6-trifluoromethyl-2,4(1H,3H)pyrimidinedione-3-yl, 1-methyl-6-trifluoromethyl-2,4(1H,3H)pyrimidinedione-3-yl or 1-amino-6-trifluoromethyl-2,4(1H,3H) pyrimidinedione-3-yl group, characterized in that the process comprises reacting a halogenated benzene compound represented by the formula (1a):

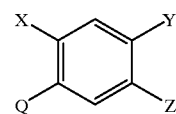

(1a)

wherein X, Z and Q are as defined above, and Y is fluorine, chlorine, bromine or iodine atom, provided that if X is fluorine atom, then Y is chlorine, bromine or iodine atom, and if X is chlorine atom, then Y is bromine or iodine atom, with one or more cyanides selected from potassium cyanide, sodium cyanide and zinc cyanide in the presence of a metallic catalyst.

[2] A process as described in the above item [1] wherein Z is $C_1$–$C_4$ alkylsulfonylamino, bis($C_1$–$C_4$ alkylsulfonyl)amino, ($C_2$–$C_5$ alkylcarbonyl)($C_1$–$C_4$ alkylsulfonyl)amino or (optionally substituted benzoyl)($C_1$–$C_4$ alkylsulfonyl)amino group.

[3] A process as described in the above item [1] wherein Z is $C_1$–$C_4$ alkylsulfonylamino group.

[4] A process as described in the above item [1] wherein Q is 6-trifluoromethyl-2,4(1H,3H)pyrimidinedione-3-yl, 1-methyl-6-trifluoromethyl-2,4(1H,3H)pyrimidinedione-3-yl or 1-amino-6-trifluoromethyl-2,4(1H,3H) pyrimidinedione-3-yl group.

[5] A process as described in the above item [2] wherein Q is 6-trifluoromethyl-2,4(1H,3H)pyrimidinedione-3-yl, 1-methyl-6-trifluoromethyl-2,4(1H,3H)pyrimidinedione-3-yl or 1-amino-6-trifluoromethyl-2,4(1H,3H) pyrimidinedione-3-yl group.

[6] A process as described in the above item [3] wherein Q is 6-trifluoromethyl-2,4(1H,3H)pyrimidinedione-3-yl, 1-methyl-6-trifluoromethyl-2,4(1H,3H)pyrimidinedione-3-yl or 1-amino-6-trifluoromethyl-2,4(1H,3H) pyrimidinedione-3-yl group.

[7] A process as described in the above items [1] to [6] wherein palladium, nickel or platinum is used as the metallic catalyst.

[8] A process as described in the above items [1] to [6] wherein palladium is used as the metallic catalyst.

[9] A process as described in the above items [7] and [8] wherein a metal selected from zinc, iron, manganese, tin, copper, magnesium, chromium, titanium and aluminum or a halide of the metal is used as a co-catalyst.

[10] A process as described in the above items [7] and [8] wherein a halide of a metal selected from zinc, tin and copper is used as a co-catalyst.

DETAILED DESCRIPTION OF THE PREFERRED EMBODIMENTS

The process of the present invention will be described in more detail. Scheme of the process of the present invention is as follows:

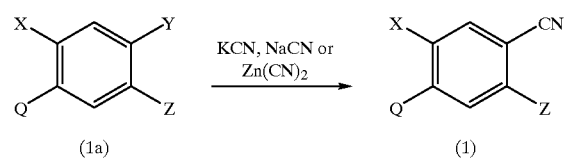

wherein X, Y, Z and Q are as defined above.

In the process of the present invention, examples of Z include nitro, amino, methylsulfonylamino, ethylsulfonylamino, n-propylsulfonylamino, i-propylsulfonylamino, n-butylsulfonylamino, i-butylsulfonylamino, s-butylsulfonylamino, tert-butylsulfonylamino, bis(methylsulfonyl)amino, bis(ethylsulfonyl)amino, bis(n-propylsulfonyl)amino, bis(i-propylsulfonyl)amino, bis(n-butylsulfonyl)amino, bis(i-butylsulfonyl)amino, bis(s-butylsulfononyl)amino, bis(tert-butylsulfonyl)amino, methoxycarbonylamino, ethoxycarbonylamino, n-propoxycarbonylamino, i-propoxycarbonylamino, n-butoxycarbonylamino, i-butoxycarbonylamino, s-butoxycarbonylamino, tert-butoxycarbonylamino, acetylamino, propionylamino, n-butyrylamino, i-butyrylamino, benzoylamino, 2-bromobenzoylamino, 3-bromobenzoylamino, 4-bromobenzoylamino, 2-chlorobenzoylamino, 3-chlorobenzoylamino, 4-chlorobenzoylamino, 2-fluorobenzoylamino, 3-fluorobenzoylamino, 4-fluorobenzoylamino, 2-toluoylamino, 3-toluoylamino, 4-toluoylamino, 2-ethylbenzoylamino, 4-ethylbenzoylamino, 2-i-propylbenzoylamino, 4-i-propylbenzoylamino, 2-tert-butylbenzoylamino, 4-tert-butylbenzoylamino, 2-methoxybenzoylamino, 3-methoxybenzoylamino, 4-methoxybenzoylamino, 2-ethoxybenzoylamino, 3-ethoxybenzoylamino, 4-ethoxybenzoylamino, 2-i-propyloxybenzoylamino, 3-i-propyloxybenzoylamino, 4-i-propyloxybenzoylamino, 2-n-butoxybenzoylamino, 3-n-butoxybenzoylamino, 4-n-butoxybenzoylamino, acetyl(methylsulfonyl)amino, propionyl(methylsulfonyl)amino, n-butyryl(methylsulfonyl)amino, i-butyryl(methylsulfonyl)amino, acetyl(ethylsulfonyl)amino, propionyl(ethylsulfonyl)amino, n-butyryl(ethylsulfonyl)amino, i-butyryl(ethylsulfonyl)amino, acetyl(n-propylsulfonyl)amino, propionyl(n-propylsulfonyl)amino, n-butyryl(n-propylsulfonyl)amino, i-butyryl(n-propylsulfonyl)amino, benzoyl(methylsulfonyl)amino, 2-bromobenzoyl(methylsulfonyl)amino, 3-bromobenzoyl(methylsulfonyl)amino, 4-bromobenzoyl(methylsulfonyl)amino, 2-chlorobenzoyl(methylsulfonyl)amino, 3-chlorobenzoyl(methylsulfonyl)amino, 4-chlorobenzoyl(methylsulfonyl)amino, 2-fluorobenzoyl(methylsulfonyl)amino, 3-fluorobenzoyl-(methylsulfonyl)amino, 4-fluorobenzoyl(methylsulfonyl)amino, 2-toluoyl(methylsulfonyl)amino, 3-toluoyl(methylsulfonyl)amino, 4-toluoyl(methylsulfonyl)amino, 2-ethylbenzoyl(methylsulfonyl)amino, 4-ethylbenzoyl(methylsulfonyl)amino, 2-i-propylbenzoyl(methylsulfonyl)amino, 4-i-propylbenzoyl(methylsulfonyl)amino, 2-tert-butylbenzoyl(methylsulfonyl)amino, 4-tert-butylbenzoyl(methylsulfonyl)amino, 2-methoxybenzoyl(methylsulfonyl)amino, 3-methoxybenzoyl (methylsulfonyl)amino, 4-methoxybenzoyl(methylsulfonyl)amino, 2-ethoxybenzoyl(methylsulfonyl)amino, 3-ethoxybenzoyl(methylsulfonyl)amino, 4-ethoxybenzoyl(methylsulfonyl)amino, 2-i-propyloxybenzoyl(methylsulfonyl)amino, 3-i-propyloxybenzoyl(methylsulfonyl)amino, 4-i-propyloxybenzoyl(methylsulfonyl)amino, 2-n-butoxybenzoyl(methylsulfonyl)amino, 3-n-butoxybenzoyl(methylsulfonyl)amino, 4-n-butoxybenzoyl(methylsulfonyl)amino, benzoyl(ethylsulfonyl)amino, 2-bromobenzoyl(ethylsulfonyl)amino, 3-bromobenzoyl(ethylsulfonyl)amino, 4-bromobenzoyl(ethylsulfonyl)amino, 2-chlorobenzoyl(ethylsulfonyl)amino, 3-chlorobenzoyl(ethylsulfonyl)amino, 4-chlorobenzoyl(ethylsulfonyl)amino, 2-fluorobenzoyl(ethylsulfonyl)amino, 3-fluorobenzoyl(ethylsulfonyl)amino, 4-fluorobenzoyl(ethylsulfonyl)amino, 2-toluoyl(ethylsulfonyl)amino, 3-toluoyl(ethylsulfonyl)amino, 4-toluoyl(ethylsulfonyl)amino, 2-ethylbenzoyl(ethylsulfonyl)amino, 4-ethylbenzoyl(ethylsulfonyl)amino, 2-i-propylbenzoyl(ethylsulfonyl)amino, 4-i-propylbenzoyl(ethylsulfonyl)amino, 2-tert-butylbenzoyl(ethylsulfonyl)amino, 4-tert-butylbenzoyl(ethylsulfonyl)amino, 2-methoxybenzoyl(ethylsulfonyl)amino, 3-methoxybenzoyl(ethylsulfonyl)amino, 4-methoxybenzoyl(ethylsulfonyl)amino, 2-ethoxybenzoyl(ethylsulfonyl)amino, 3-ethoxybenzoyl(ethylsulfonyl)amino, 4-ethoxybenzoyl(ethylsulfonyl)amino, 2-i-propyloxybenzoyl(ethylsulfonyl)amino, 3-i-propyloxybenzoyl(ethylsulfonyl)amino, 4-i-propyloxybenzoyl(ethylsulfonyl)amino, 2-n-butoxybenzoyl(ethylsulfonyl)amino, 3-n-butoxybenzoyl(ethylsulfonyl)amino, 4-n-butoxybenzoyl(ethylsulfonyl)amino, benzoyl(n-propylsulfonyl)amino, 2-bromobenzoyl(n-propylsulfonyl)amino, 3-bromobenzoyl(n-propylsulfonyl)amino, 4-bromobenzoyl(n-propylsulfonyl)amino, 2-chlorobenzoyl(n-propylsulfonyl)amino, 3-chlorobenzoyl(n-propylsulfonyl)amino, 4-chlorobenzoyl(n-propylsulfonyl)amino, 2-fluorobenzoyl(n-propylsulfonyl)amino, 3-fluorobenzoyl(n-propylsulfonyl)amino, 4-fluorobenzoyl(n-propylsulfonyl)amino, 2-toluoyl(n-propylsulfonyl)amino, 3-toluoyl(n-propylsulfonyl)amino, 4-toluoyl(n-propylsulfonyl)amino, 2-ethylbenzoyl(n-propylsulfonyl)amino, 4-ethylbenzoyl(n-propylsulfonyl)amino, 2-i-propylbenzoyl(n-propylsulfonyl)amino, 4-i-propylbenzoyl(n-propylsulfonyl)amino, 2-tert-butylbenzoyl(n-propylsulfonyl)amino, 4-tert-butylbenzoyl(n-propylsulfonyl)amino, 2-methoxybenzoyl(n-propylsulfonyl)amino, 3-methoxybenzoyl(n-propylsulfonyl)amino, 4-methoxybenzoyl(n-propylsulfonyl)amino, 2-ethoxybenzoyl(n-propylsulfonyl)amino, 3-ethoxybenzoyl(n-propylsulfonyl)amino, 4-ethoxybenzoyl(n-propylsulfonyl)amino, 2-i-propyloxybenzoyl(n-propylsulfonyl)amino, 3-i-propyloxybenzoyl(n-propylsulfonyl)amino, 4-i-propyloxybenzoyl(n-propylsulfonyl)amino, 2-n-butoxybenzoyl(n-propylsulfonyl)amino, 3-n-butoxybenzoyl(n-propylsulfonyl)amino and 4-n-butoxybenzoyl(n-propylsulfonyl)amino groups and the like. Among them, $C_1$–$C_4$ alkylsulfonylamino, bis($C_1$–$C_4$ alkylsulfonyl)amino, ($C_2$–$C_5$ alkylcarbonyl)($C_1$–$C_4$ alkylsulfonyl)amino and (optionally substituted benzoyl)($C_1$–$C_4$ alkylsulfonyl)amino groups are preferable, $C_1$–$C_4$ alkylsulfonylamino group being more preferable.

Examples of Q include hydrogen atom, and nitro, amino, methoxycarbonylamino, ethoxycarbonylamino, n-propoxycarbonylamino, i-propoxycarbonylamino, n-butoxycarbonylamino, i-butoxycarbonylamino, s-butoxycarbonylamino, tert-butoxycarbonylamino, 6-trifluoromethyl-2,4(1H,3H)pyrimidinedione-3-yl, 1-methyl-6-trifluoromethyl-2,4(1H,3H)pyrimidinedione-3-yl and 1-amino-6-trifluoromethyl-2,4(1H,3H)pyrimidinedione-3-yl groups and the like. Among them, 6-trifluoromethyl-2,4(1H,3H)pyrimidinedione-3-yl, 1-methyl-6-trifluoromethyl-2,4(1H,3H)pyrimidinedione-3-yl and 1-amino-6-trifluoromethyl-2,4(1H,3H) pyrimidinedione-3-yl groups are preferable.

With respect to one mole of the halogenated benzene compound (1a) as a starting substance, potassium or sodium cyanide is generally used in an amount of 0.5 to 10 moles, preferably 0.8 to 3 moles and zinc cyanide is generally used in an amount of 0.25 to 10 moles, preferably 0.4 to 1.5 moles. These metal cyanides may be used in combination.

Examples of the metallic catalyst include iron, cobalt, nickel, ruthenium, rhodium, palladium, iridium, platinum, osmium and the like. Nickel, palladium and platinum are preferable, palladium being more preferable. Specifically, the nickel catalyst is a supported catalyst such as nickel supported on silica, nickel supported on alumina and nickel supported on carbon; a complex catalyst such as dichlorobis(triphenylphosphine)nickel, dichloro[1,2-bis(diphenylphosphino)ethane]nickel, dichloro[1,3-bis(diphenylphosphino)propane]nickel, dichlorobis[1,4-bis(diphenylphosphino)butane]nickel, dichlorobis[1,1'-

(diphenylphosphino)ferrocene]nickel, dibromobis(triphenylphosphine)nickel, dibromo[1,2-bis(diphenylphosphino)ethane]nickel, dibromo[1,3-bis(diphenylphosphino)propane]nickel, dibromobis[1,4-bis(diphenylphosphino)butane]nickel, dibromobis[1,'-(diphenylphosphino)ferrocene]nickel, bromobis(triphenylphosphine)nickel, chlorobis(triphenylphosphine)nickel, tris(triphenylphosphine)nickel, bis(triphenylphosphine)dicarbonylnickel, tetrakis(triphenylphosphine)nickel, tetrakis(triphenylphosphite)nickel, bis(cyclooctadiene)nickel and acetylacetonato nickel; and nickel chloride, nickel bromide, nickel iodide, nickel nitrate, nickel acetate, nickel oxide, nickel cyanide, and the like.

The palladium catalyst is a supported catalyst such as palladium supported on silica, palladium supported on alumina and palladium supported on carbon; a complex catalyst such as (2,2-bipyridine)dichloropalladium, bis(acetonitrile)palladium chloride, bis(benzonitrile)palladium chloride, bis[1,2-(diphenylphosphino)ethane]palladium, bis[1,2-bis(diphenylphosphino)ethane]palladium chloride, dichlorobis(triphenylphosphine)palladium, dichlorobis(trimethylphosphine)palladium, dichlorobis(tributylphosphine)palladium, tetrakis(triethylphosphite)palladium, bis(cycloocta-1,5-diene)palladium, tetrakis(triphenylphosphine)palladium, dicarbonylbis(triphenylphosphine)palladium, carbonyltris(triphenylphosphine)palladium, acetylacetonato palladium, dichloro(1,5-cyclooctadiene)palladium and tris(dibenzylideneacetone)dipalladium; and palladium chloride, palladium bromide, palladium nitrate, palladium oxide, palladium acetate, palladium cyanide, and the like.

The platinum catalyst is a supported catalyst such as platinum supported on silica, platinum supported on alumina and platinum supported on carbon; a complex catalyst such as bis(acetonitrile)dichloroplatinum, bis(benzonitrile)dichloroplatinum, dichlorobis(triphenylphosphine)platinum, dichlorobis(trimethylphosphine)platinum, dichlorobis(tributylphosphine)platinum, tetrakis(triphenylphosphine)platinum, tetrakis(triphenylphosphite)platinum, tris(triphenylphosphine)platinum, dicarbonylbis(triphenylphosphine)platinum, bis(triphenylphosphine)(ethylene)platinum, carbonyltris(triphenylphosphine)platinum, bis(1,5-cyclooctadiene)platinum, (1,5-cyclooctadiene)dichloroplatinum and (1,5-cyclooctadiene)dibromoplatinum; and platinum chloride, platinum bromide, platinum iodide, platinum oxide and the like.

The above catalysts may be used singly or in combination.

The catalyst is generally used in an amount of 0.0001 to 100 molar %, preferably 0.01 to 50 molar % with respect to the compound of the general formula (1a).

If necessary, a ligand may be added to the metallic catalyst in order to stabilize and activate the catalyst.

The ligand is exemplified below. As mono- or multidentate tertiary phosphines, bis(dialkylphosphino)alkanes such as 1,1-bis(dimethylphosphino)methane, 1,1-bis(diethylphosphino)methane, 1,2-bis(dimethylphosphino)ethane, 1,2-(diethylphosphino)ethane, 1,3-bis(dimethylphosphino)propane and 1,4-bis(dimethylphosphino)butane; bis(diphenylphosphino)alkanes such as 1,1-bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane and 1,6-bis(diphenylphosphino)hexane; and. 1,1'-bis(diphenylphosphino)ferrocene, tris(3-sulfonatophenyl)phosphine sodium salt, bis(diphenylphosphino)binaphthyl, trimethylphosphine, triethylphosphine, tributylphosphine, triphenylphosphine, tris(para-tolyl)phosphine, tris(parafluorophenyl)phosphine, tris(2,6-dimethylphenyl)phosphine, sodium diphenylphosphinobenzene-3-sulfonate, bis(3-sulfonatophenyl)phosphinobenzene sodium salt, 17-diphenylphosphino-2,5,8,11,14-pentaoxabicyclo-[13.4.0]-nonadeca-15,17,19-triene and 20-diphenylphosphino-2,5,8,11,14,17-hexaoxabicyclo-[16.4.0]-docosa-18,20,22-triene, and the like are mentioned.

As other ligands, phosphonic esters such as triethyl phosphite, tributyl phosphite, triphenyl phosphite and tris(2,6-dimethylphenyl)phosphite; phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphoniuim bromide and tetraphenylphosphonium chloride; phosphoric esters such as triphenyl phosphate, trimethyl phosphate, triethyl phosphate and triallyl phosphate; phosphine oxides such as triphenylphosphine oxide and diphenylmethylphosphine oxide; phosphine sulfides such as triphenylphosphine sulfide and diphenylmethylphosphine sulfide; unsaturated hydrocarbons such as cyclooctadiene and cyclopentadiene; nitriles such as benzonitrile and acetonitrile; pyridine alanogs such as 2,2'-bipyridine, 1,10-phenanthroline and 8-hydroxyquinoline; acetylacetone, and the like are mentioned.

The ligand is generally used in an amount of 0 to 10,000 molar %, preferably 0 to 1,000 molar % with respect to the metallic catalyst.

According to the present invention, the metallic catalysts and the phosphines may be added to a reaction system in combination or separately, or alternatively they may be used as a complex previously formed.

For reducing a divalent metallic complex to a corresponding zero-valent complex, zinc powder, tin powder, manganese powder, magnesium powder, cobalt powder and iron powder, iron(II) salt, tin(II) salt, manganese(III) salt, cobalt (II) salt, formic acid and oxalic acid, and a mixture thereof, and an alloy powder thereof, and, a Grignard reagent such as ethyl magnesium bromide, an alkyl lithium reagent such as butyl lithium, a metallic reagent for hydrogenation such as sodium borohydride, and an electrolytic reduction may be used.

Examples of an organic solvent used in the process of the present invention include aromatic hydrocarbons such as benzene, toluene, xylene and chlorobenzene; halogenated hydrocarbons such as chloroform and methylene chloride; nitrites such as acetonitrile and propionitrile; ketones such as acetone, methyl ethyl ketone and methyl isobutyl ketone; ethers such as diethyl ether, dioxane, tetrahydrofuran and dimethoxyethane; tertiary amines such as pyridine, 5-ethyl-2-methylpyridine, quinoline and N,N'-dimethylaniline; acid amides such as N,N'-dimethylacetamide, N,N'-dimethylformamide, N-methylpyrrolidone and tetramethylurea; sulfur-containing compounds such as dimethylsulfoxide and sulfolane; phosphoric compounds such as hexamethylphosphoric triamide; and the like. Two or more of them may be mixed to use.

In order to proceed the reaction more smoothly, the use of a co-catalyst is effective. Examples of the co-catalyst include metal salts such as copper(I) chloride, copper(I) bromide, copper(I) iodide, copper(II) chloride, copper(II) oxide, copper(II) sulfate, copper(I) cyanide, copper powder, zinc (II) chloride, zinc(II) bromide, zinc(II) iodide, zinc(II) cyanide, zinc powder, tin(II) chloride, tin(II) bromide, tin(II) iodide, tin powder, aluminum oxide, aluminum chloride, iron(II) chloride, iron(III) chloride, iron powder, magnesium (II) chloride, chromium(II) chloride, manganese (II) chloride, lead(IV) acetate, titanium(IV) chloride, potassium hexachloroplatinate(IV) and potassium hexacyanoferrate (III); crown ethers such as 18-crown-6-ether, 15-crown-5-ether and dicyclohexyl-18-crown-6-ether; and silicon tetrachloride. Optionally, sodium iodide, sodium bromide, potassium iodide, potassium bromide or the like may be added to the reaction system. Among the co-catalysts mentioned above, the halides of the metal selected from zinc, iron, manganese, tin, copper, magnesium, chromium, titanium and aluminum are the preferable co-catalysts. The more preferable co-catalysts are the halides of the metal selected from zinc, tin and copper. The amount of the co-catalyst to be added is generally 0 to 10,000 molar %, preferably 0 to 500 molar % with respect to the metal catalyst.

Generally, the reaction is carried out at a temperature of from room temperature to 300° C., preferably 50 to 200° C. Alternatively, it may be carried out at a reflux temperature of the solvent to be used. Generally, reaction time ranges from 30 minutes to 72 hours, preferably 1 to 24 hours.

EXAMPLES

The process of the present invention will be described in more detail by referring to the following Examples which are not intended to limit the invention.

Reaction scheme according to the Examples is set forth below.

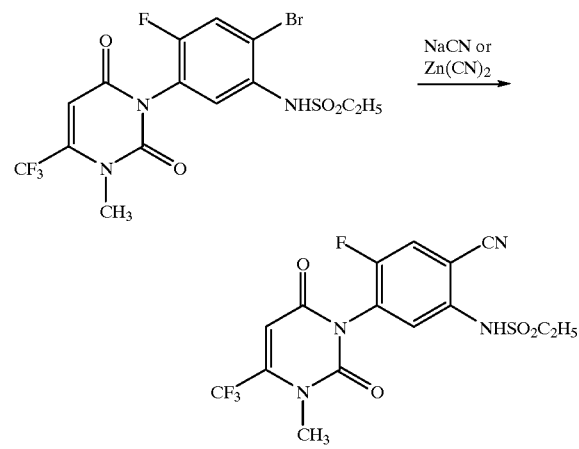

Example 1

Preparation of 3-(4-cyano-5-ethylsulfonylamino-2-fluorophenyl)-1-methyl-6-trifluoromethyl-2,4(1H,3H)-pyrimidinedione (Compound No. 1)

1.2 g (2.5 mmol) of 3-(4-bromo-5-ethylsulfonylamino-2-fluorophenyl)-1-methyl-6-trifluoromethyl-2,4(1H,3H)pyrimidinedione, 0.15 g of sodium cyanide and 0.04 g of zinc chloride were added to 5 ml of 5-ethyl-2-picoline and the mixture was stirred at 120° C. under an argon atmosphere for 1 hour. Next, 0.6 g of tetrakis(triphenylphosphine)palladium was added to the mixture, which was then heated with stirring for 10 hours. After the reaction was completed, the title compound was obtained with a yield of 90% as determined by the internal standard method in liquid chromatography.

Example 6

Preparation of 3-(4-cyano-5-ethylsulfonylamino-2-fluorophenyl)-1-methyl-6-trifluoromethyl-2,4(1H,3H)-pyrimidinedione (Compound No. 1)

1.2 g (2.5 mmol) of 3-(4-bromo-5-ethylsulfonylamino-2-fluorophenyl)-1-methyl-6-trifluoromethyl-2,4(1H,3H)pyrimidinedione and 0.11 g of 55% sodium hydride in oil were added to 20 g of 5-ethyl-2-picoline and the mixture was stirred at room temperature for 30 minutes. Next, 0.07 g of copper(II) chloride and 0.15 g of sodium cyanide were added to the mixture, which was then stirred at 140° C. under an argon atmosphere for 1 hour. Further, 0.3 g of tetrakis(triphenylphosphine)palladium was added to the mixture, which was then heated with stirring for 3 hours. After the reaction was completed, 79% of the title compound was detected as the relative area value in liquid chromatography.

Example 7

Preparation of 3-(4-cyano-5-ethylsulfonylamino-2-fluorophenyl)-1-methyl-6-trifluoromethyl-2,4(1H,3H)-pyrimidinedione (Compound No. 1)

0.5 g (1.0 mmol) of 3-(4-bromo-5-ethylsulfonylamino-2-fluorophenyl)-1-methyl-6-trifluoromethyl-2,4(1H,3H) pyrimidinedione was dissolved in 10 ml of 5-ethyl-2-picoline, to which 0.04 g of sodium hydride was added under cooling with ice, and the mixture was stirred for 5 minutes. Next, 0.04 g of palladium acetate and 0.16 g of 1,4-bis(diphenylphosphino)ethane were added to the mixture, which was then stirred at 90° C. under an argon atmosphere for 1 hour. After the mixture was allowed to cool, 0.03 g of zinc chloride and 0.06 g of sodium cyanide were added to the mixture, which was then stirred for further 4 hours. After the reaction was completed, 61% of the title compound was detected as the relative area value in liquid chromatography.

Example 9

Preparation of 3-(4-cyano-5-ethylsulfonylamino-2-fluorophenyl)-1-methyl-6-trifluoromethyl-2,4(1H,3H)-pyrimidinedione (Compound No. 1)

2.0 g (4.2 mmol) of 3-(4-bromo-5-ethylsulfonylamino-2-fluorophenyl)-1-methyl-6-trifluoromethyl-2,4(1H,3H) pyrimidinedione, 0.3 g of zinc cyanide and 0.5 g of tetrakis(triphenylphosphine)palladium were added to 10 g of 5-ethyl-2-picoline and the mixture was stirred at 80° C. under an argon atmosphere for 3.5 hours. After the reaction was completed, 94% of the title compound was detected as the relative area value in liquid chromatography.

Other Examples together with the above Examples were shown in Table 2. Any compound wherein the benzene ring was cyanized at 2-position was hardly detected in all of Examples 1 to 9.

Abbreviations and terms used in Table 2 have meanings as described in Table 1.

TABLE 1

| Abbreviation or Term | Meaning |
|---|---|
| Sub. 1 (Substrate 1) | 3-(4-bromo-5-ethylsulfonyl-amino-2-fluorophenyl)-1-methyl-6-trifluoromethyl-2,4(1H, 3H)pyrimidinedione |
| Sub. 1-Na (Substrate 1-Na) | 3-(4-bromo-5-ethylsulfonyl-amino-2-fluorophenyl)-1-methyl-6-trifluoromethyl-2,4(1H, 3H)pyrimidinedione sodium salt |
| dppe | 1,2-bis(diphenylphosphino)ethane |
| MEP | 5-ethyl-2-picoline |
| DMF | N,N-dimethylformamide |
| amount of cyanizing agent | equivalent of the cyanizing agent with respect to the substrate |

TABLE 1-continued

| Abbreviation or Term | Meaning |
| --- | --- |
| amount of catalyst | equivalent of the catalyst with respect to the substrate |
| amount of co-catalyst | equivalent of the co-catalyst with respect to the substrate |
| amount of solvent | parts by weight of the solvent per 1 part by weight of the substrate |

TABLE 2

| | Substrate | | Cyanizing Agent | | Catalyst | | Co-catalyst | | Solvent | | Reaction | | Yield*2 (%) |
| | type | amount (mmol) | type | amount (eq) | type | amount (eq) | type | amount (eq) | type | amount (part) | temp. (° C.) | time (hr) | |
| --- | --- | --- | --- | --- | --- | --- | --- | --- | --- | --- | --- | --- | --- |
| Ex. 1 | Sub. 1 | 2.5 | NaCN | 1.2 | Pd(PPh$_3$)$_4$ | 0.2 | ZnCl$_2$ | 0.2 | MEP | 4.0 | 120 | 10.0 | 90 |
| Ex. 2 | Sub. 1 | 2.5 | NaCN | 1.2 | Pd(PPh$_3$)$_4$ | 0.2 | Zn(CN)$_2$ | 0.2 | MEP | 4.0 | 100 | 3.0 | 62 |
| Ex. 3 | Sub. 1-Na | 2.5 | NaCN | 1.2 | Pd(PPh$_3$)$_4$ | 0.1 | SnCl$_2$ | 0.2 | MEP | 16.0 | 140 | 18.0 | (61) |
| Ex. 4 | Sub. 1-Na | 2.5 | NaCN | 1.2 | Pd(PPh$_3$)$_4$ | 0.1 | Cu | 0.2 | MEP | 16.0 | 140 | 3.0 | (56) |
| Ex. 5 | Sub. 1-Na | 2.5 | NaCN | 1.2 | Pd(PPh$_3$)$_4$ | 0.1 | CuCl | 0.2 | MEP | 16.0 | 140 | 3.0 | (75) |
| Ex. 6 | Sub. 1-Na | 2.5 | NaCN | 1.2 | Pd(PPh$_3$)$_4$ Pd(OAc)$_2$ | 0.1 0.2 | CuCl$_2$ | 0.2 | MEP | 16.0 | 140 | 3.0 | (79) |
| Ex. 7 | Sub. 1-Na | 1 | NaCN | 1.2 | dppe | 0.4 | ZnCl$_2$ | 0.2 | MEP | 18.0 | 140 | 4.0 | (61)*1 |
| Ex. 8 | Sub. 1-Na | 1 | NaCN | 1.2 | Pd(CN)$_2$ | 0.1 | - | - | DMF | 40.0 | 140 | 2 | (48) |
| Ex. 9 | Sub. 1 | 4.2 | Zn(CN)$_2$ | 0.6 | Pd(PPh$_3$)$_4$ | 0.1 | - | - | MEP | 5.0 | 80 | 3.5 | (94) |

Examples 1 to 9 were carried out under an Ar atmosphere.
*1: Before the addition of NaCN, stirring was carried out at 90° C. for one hour.
*2: Determined by the internal standard method.
(): relative area value on liquid chromatogram Effect of the Invention According to the process of the present invention, the benzonitrile compounds useful as herbicides and their intermediates can be obtained with a high yield.

What is claimed is:

1. A process for the preparation of benzonitrile compounds having the formula (1):

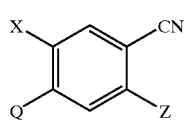

(1)

wherein:

X is hydrogen, fluorine or chlorine;

Z is $C_1$–$C_4$ alkylsulfonylamino, bis ($C_1$–$C_4$ alkylsulfonyl) amino, ($C_2$–$C_5$ alkoxycarbonyl)amino, ($C_2$–$C_5$ alkylcarbonyl)amino, (optionally substituted benzoyl) amino, ($C_2$–$C_5$ alkylcarbonyl) ($C_1$–$C_4$ alkylsulfonyl) amino or (optionally substituted benzoyl) ($C_1$–$C_4$ alkylsulfonyl)amino; and Q is 6-trifluoromethyl-2,4(1H, 3H)-pyrimidinedione-3-yl, 1-methyl-6-trifluoromethyl-2,4(1H, 3H)pyrimidinedione-3-yl or 1-amino-6-trifluoromethyl-2,4(1H, 3H)pyrimidinedione-3-yl group, which process comprises reacting a halogenated benzene compound having the formula (1a):

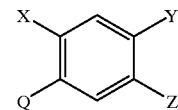

(1a)

wherein X, Z and Q are as defined above; and Y is fluorine, chlorine, bromine or iodine; provided that if X is fluorine, then Y is chlorine, bromine or iodine; and if X is chlorine; then Y is bromine or iodine; with one or more cyanides selected from the group consisting of potassium cyanide, sodium cyanide and zinc cyanide in the presence of a metallic catalyst, comprising:

iron, cobalt, nickel, ruthenium, rhodium, palladium, iridium, platinum, or osmium.

2. The process as claimed in claim 1, wherein Z is $C_1$–$C_4$ alkylsulfonylamino, bis($C_1$–$C_4$ alkylsulfonyl)amino, ($C_2$–$C_5$ alkylcarbonyl) ($C_1$–$C_4$ alkylsulfonyl)amino or (optionally substituted benzoyl) ($C_1$–$C_4$ alkylsulfonyl) amino.

3. The process as claimed in claim 1, wherein Z is $C_1$–$C_4$ alkylsulfonylamino.

4. The process as claimed in claim 1, wherein the metallic catalyst comprises palladium, nickel or platinum.

5. The process as claimed in claim 4, wherein palladium is used as the metallic catalyst.

6. The process as claimed in claim 1, wherein the metallic catalyst further comprises a metal comprising zinc, iron, manganese, tin, copper, magnesium, chromium, titanium or aluminum or a halide or cyanide thereof.

7. The process as claimed in claim 1, wherein the metallic catalyst further comprises a halide of zinc, tin or copper.

8. The process as claimed in claim 1, wherein from 0.5 to 10 moles of the cyanide are used per mole of the halogenated benzene compound.

9. The process as claimed in claim 4, wherein said metallic catalyst is a supported catalyst.

10. The process as claimed in claim 9, wherein said metallic catalyst is supported in silica, alumina or carbon.

11. The process as claimed in claim 4, wherein said metallic catalyst is a complex catalyst.

12. The process as claimed in claim 1, wherein said metallic catalyst further comprises a ligand.

13. The process as claimed in claim 1, which is conducted at from room temperature to 300° C.

14. The process as claimed in claim 13, which is conducted at from 50 to 200° C.

15. The process as claimed in claim 11, wherein said complex catalyst is selected from the group consisting of palladium acetate ($Pd(OAc)_2$), palladium cyanide ($Pb(CN)_2$), and tetrakis (triphenylphosphine) palladium.

16. The process as claimed in claim 6, wherein said halide or cyanide is selected from the group consisting of $ZnCl_2$, $Zn(CN)_2$, $SnCl_2$, $CuCl$ and $CuCl_2$.

* * * * *

UNITED STATES PATENT AND TRADEMARK OFFICE
CERTIFICATE OF CORRECTION

PATENT NO. : 6,331,628 B1
DATED : December 18, 2001
INVENTOR(S) : Yasuo Kondo et al.

It is certified that error appears in the above-identified patent and that said Letters Patent is hereby corrected as shown below:

<u>Column 9,</u>
Table 2, under heading "type", third occurrence, "Pd(OAc)$_2$ move one
    dppe"
line down to line up with "1.2" under column heading "amount
    (eq)".
Table 2, under heading "Solvent" move")" down one line to be adjacent to "(part".

Signed and Sealed this

Third Day of September, 2002

Attest:

Attesting Officer

JAMES E. ROGAN
Director of the United States Patent and Trademark Office